(12) United States Patent
Gellert

(10) Patent No.: US 9,027,421 B2
(45) Date of Patent: May 12, 2015

(54) LIQUID-METERING DEVICE FOR A GAS ANALYZER

(75) Inventor: Udo Gellert, Bartlesville, OK (US)

(73) Assignee: Siemens Aktiengesellschaft, Munich (DE)

( * ) Notice: Subject to any disclaimer, the term of this patent is extended or adjusted under 35 U.S.C. 154(b) by 518 days.

(21) Appl. No.: 13/518,348

(22) PCT Filed: Dec. 21, 2010

(86) PCT No.: PCT/EP2010/070342
§ 371 (c)(1),
(2), (4) Date: Nov. 6, 2012

(87) PCT Pub. No.: WO2011/076774
PCT Pub. Date: Jun. 30, 2011

(65) Prior Publication Data
US 2013/0175356 A1    Jul. 11, 2013

(30) Foreign Application Priority Data

Dec. 22, 2009  (DE) .......................... 10 2009 059 963

(51) Int. Cl.
*G01N 1/38* (2006.01)
*B05B 5/00* (2006.01)
(Continued)

(52) U.S. Cl.
CPC *B05B 5/00* (2013.01); *G01N 30/04* (2013.01); *G01N 30/12* (2013.01); *G01N 30/24* (2013.01); *G01N 30/72* (2013.01); *G01N 30/7246* (2013.01)

(58) Field of Classification Search
CPC .............. G01N 30/24; G01N 30/7246; G01N 35/1016; G01N 2030/8447; B05B 5/001; B05B 5/00

USPC ................................ 73/864.81; 95/89; 96/105
See application file for complete search history.

(56) References Cited

U.S. PATENT DOCUMENTS 3,366,149 A * 1/1968 Taft et al. .......................... 141/82
3,455,817 A * 7/1969 Modell ............................ 210/640
(Continued)

FOREIGN PATENT DOCUMENTS

| CN | 1790209 A | 6/2006 |
|----|-----------|--------|
| DE | 10047341 | 2/2001 |

(Continued)

OTHER PUBLICATIONS

PCTEP2010070342 English Translation of the Written Opinion of the International Searching Authority, Jul. 5, 2012.*

*Primary Examiner* — Lisa Caputo
*Assistant Examiner* — Punam Roy
(74) *Attorney, Agent, or Firm* — Cozen O'Connor

(57) ABSTRACT

A liquid-metering device comprising a droplet generator including a reservoir and, connected to the latter, a displacement space which is modifiable by an electromechanical transducer and which has an outlet opening and, upon excitation of the transducer, shoots a liquid droplet from a cold area into a heatable area through or counter to a gas stream generated by a gas source. To make the device suitable for automatic and quasi-continuous liquid metering in process analysis, a heatable evaporation chamber is provided through which the liquid to be metered flows via valves, and, between the evaporation chamber and the reservoir, a condensate chamber is connected via further valves. The condensate chamber and the reservoir are connected via additional valves and a pressure regulator to the gas source.

5 Claims, 2 Drawing Sheets

(51) Int. Cl.
   *G01N 30/04*   (2006.01)
   *G01N 30/12*   (2006.01)
   *G01N 30/24*   (2006.01)
   *G01N 30/72*   (2006.01)

(56) References Cited

U.S. PATENT DOCUMENTS

| | | | | |
|---|---|---|---|---|
| 4,405,344 | A | * | 9/1983 | Sisti et al. .................... 95/89 |
| 4,615,226 | A | * | 10/1986 | DiNuzzo et al. ............. 73/864.87 |
| 4,958,529 | A | * | 9/1990 | Vestal ........................ 73/864.81 |
| 5,252,109 | A | * | 10/1993 | Munari et al. ................... 95/87 |
| 5,266,192 | A | * | 11/1993 | Ligon et al. ................ 210/198.2 |
| 5,306,412 | A | * | 4/1994 | Whitehouse et al. .......... 204/452 |
| 5,359,196 | A | * | 10/1994 | Whitt ............................ 250/288 |
| 5,736,741 | A | * | 4/1998 | Bertsch et al. ................. 250/288 |
| 6,451,614 | B1 | | 9/2002 | Grob et al. |
| 7,424,980 | B2 | * | 9/2008 | Ruediger et al. ............. 239/338 |
| 2005/0230498 | A1 | * | 10/2005 | Ruediger et al. ............. 239/338 |
| 2008/0137065 | A1 | * | 6/2008 | Oberreit et al. ................. 356/37 |

FOREIGN PATENT DOCUMENTS

| | | | | |
|---|---|---|---|---|
| DE | 10127353 | | 12/2002 | |
| DE | 10325802 | A1 * | 1/2005 | ............. B01D 1/00 |
| EP | 1063523 | A2 | 12/2000 | |
| FR | 2597631 | | 10/1987 | |

* cited by examiner

LIQUID-METERING DEVICE FOR A GAS ANALYZER

CROSS-REFERENCE TO RELATED APPLICATIONS

This is a U.S. national stage of application No. PCT/EP2010/070342 filed 21 Dec. 2010. Priority is claimed on German Application No. 10 2009 059 963.0 filed 22 Dec. 2009, the content of which is incorporated herein by reference in its entirety.

BACKGROUND OF THE INVENTION

1. Field of the Invention

The invention relates to metering devices and, more particularly, to a liquid metering device for a gas analyzer.

2. Description of the Related Art

DE 10127353 A1 discloses a conventional a liquid metering device comprising a droplet generator.

For processing or treating liquids, for example, their analysis, prior purification of the sample of dissolved components which cannot be vaporized by complete vaporization and subsequent complete condensation of the liquid can be required. Especially in process chromatography, the metering procedure is to be process capable, i.e., able to be performed automatically. The smallest liquid quantity which can be metered is to be significantly less than 0.1 μl and discrimination of the vaporized liquid sample, for example, in the form of local concentration differences of different vaporization components in the vapor, is to be prevented. Thus, for example, simply dripping the liquid into a heated vaporization space results in uneven vaporization, because each individual droplet vaporizes in a fractionated manner in a time determined by droplet size and external circumstances. Here, ingredients having a low boiling point vaporize first and ingredients having a high boiling point vaporize last.

Therefore, in conventional liquid metering devices, a droplet generator is provided which, upon excitation, shoots a liquid droplet counter to a gas stream from a cold area into a heatable area, e.g., a capillary tube. The droplet generator has a reservoir and a displacement space which can be modified by an electromechanical transducer, e.g., a piezo transducer, and which has an outlet opening for the droplets.

Ultrasmall droplets having a volume of, for example, 50 μl may be generated using the droplet generator, which shoots the liquid in droplets at high speed. As a result, ultrasmall liquid quantities may also be precisely metered via the number of the droplets to be generated. The droplets shot into the heatable area vaporize rapidly and completely therein. Here, no discrimination of the liquid sample occurs because of the very small droplet size and the unsplit operating mode. Liquid that unintentionally swells out of the outlet opening of the droplet generator is disposed of by the gas stream and does not reach the capillary tube.

SUMMARY OF THE INVENTION

It is therefore an object of the invention to provide a liquid metering device that is configured to provide automatic and quasi-continuous liquid metering in process analytics.

This and other objects and advantages are achieved in accordance with the invention by a liquid metering device in which the liquid to be metered, which is taken from a process, for example, is periodically conducted into the vaporization chamber and vaporized therein. The vapor or the already formed condensate is conducted into the condensate chamber, so that only liquid components that can be vaporized are still present therein. During the vaporization and subsequent condensation of the liquid to be metered, spaces and chambers not used for this purpose are flushed using the gas, e.g., the carrier gas of a gas chromatograph, in order to remove still present liquid residues. Subsequently, with the aid of the gas, the condensate is transferred into the spaces and chambers required for the droplet generation, while simultaneously the vaporization chamber is refilled with liquid. The respective gas and liquid paths through the valves are decoupled from one another. The gas is used for flushing, conveying the liquid and, in conjunction with the pressure regulating unit, setting the pressure conditions inside the liquid metering device.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For further explanation of the invention, reference is made hereafter to the drawing, in the figures.

DETAILED DESCRIPTION OF THE PREFERRED EMBODIMENTS

Figure 1:
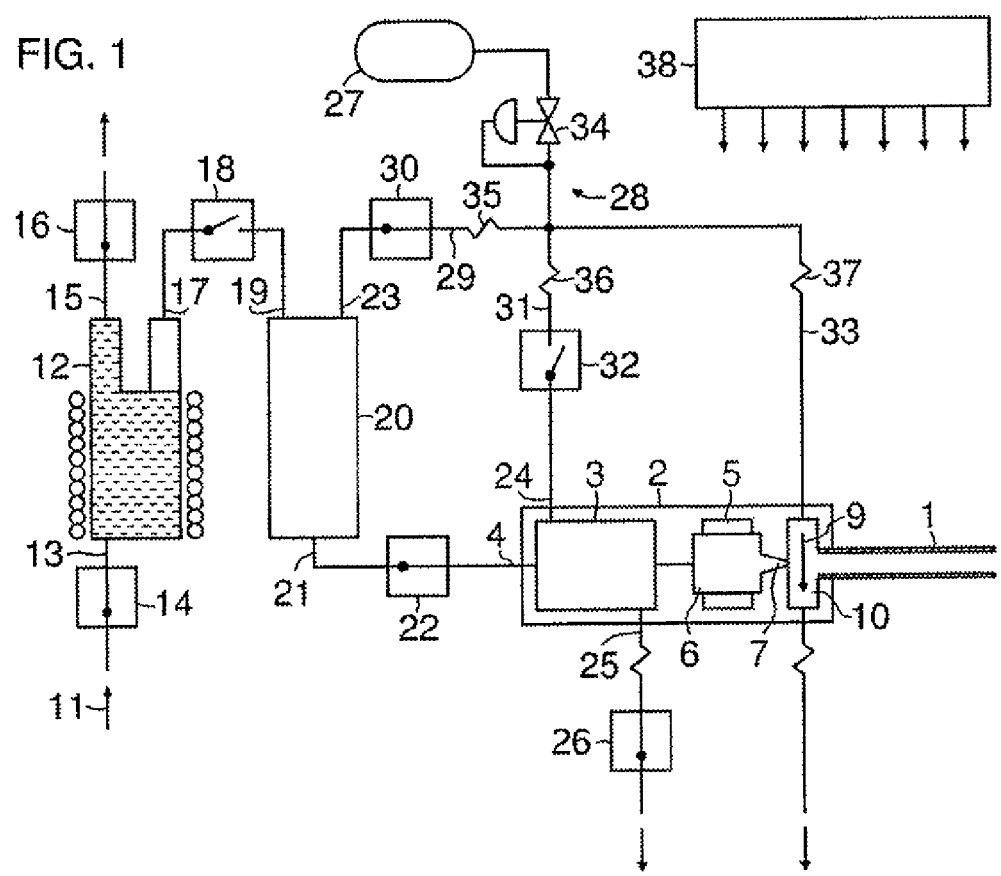
FIGS. 1 to 4 show a schematic view of an exemplary embodiment of the device according to the invention in four successive operating phases.

The liquid metering device shown in FIGS. 1 to 4 for a gas analyzer, of which only a heatable capillary 1 is visible here, has a droplet generator 2 having a reservoir 3 having liquid inlet 4 and a displacement space 6, which is connected to the reservoir 3 and can be modified by an electromechanical transducer 5 and has an outlet opening 7. Upon excitation of the transducer 5, a liquid droplet 8 (see FIG. 4) or a sequence thereof is shot from the displacement space 6 through or, as is known from DE 10127353 A1, counter to a gas stream 9 from a cold area 10 into a heatable area, i.e., the capillary 1 here.

The liquid 11 to be metered and subsequently to be analyzed is taken from a process and conducted through a heatable vaporization chamber 12. The vaporization chamber 12 has a liquid supply 13 having a first valve 14 and a liquid drain 15 having a second valve 16 for this purpose. The vaporization chamber 12 is connected to a vapor or condensate inlet 19 of a condensate chamber 20 via a vapor outlet 17 and a third valve 18. The condensation can already occur in the connection between both chambers 12 and 20 or at the latest in the chamber 20. The condensate chamber 20 is connected via a condensate outlet 21 and a fourth valve 22 to the liquid inlet 4 of the reservoir 3 of the droplet generator 2. The condensate chamber 20 and the reservoir 3 of the droplet generator 2 each have a gas inlet 23 or 24 and the reservoir 3 has a liquid outlet 25 having a fifth valve 26.

A pressure regulating unit 28 is connected to a gas source 27, e.g., the carrier gas source of a gas chromatograph, the unit being connected at a first outlet 29 via a sixth valve 30 to the gas inlet 23 of the condensate chamber 20 and at a second outlet 31 via a seventh valve 32 to the gas inlet 24 of the reservoir 3 of the droplet generator 2. The gas stream 9 is provided at a third outlet 33. In the presently contemplated exemplary embodiment, the pressure regulating unit 28 consists of a pressure regulator 34 having three flow resistances 35, 36, 37 for each of the three outlets 29, 31, 33.

The seven valves 14, 16, 18, 22, 26, 30, and 32 are controlled by a control unit 38 such that the liquid metering device passes through four operating phases in each case in successive metering cycles.

FIG. 1 shows the first phase, in which the first, second, fourth, fifth, and sixth valves 14, 16, 22, 26, 30 are opened and the remaining valves 18, 32 are closed (blocked). The vaporization chamber 12 is filled with the liquid 11 to be metered. The condensate chamber 20, the reservoir 3, and the displacement space 6 are thus flushed using the gas.

Figure 2:
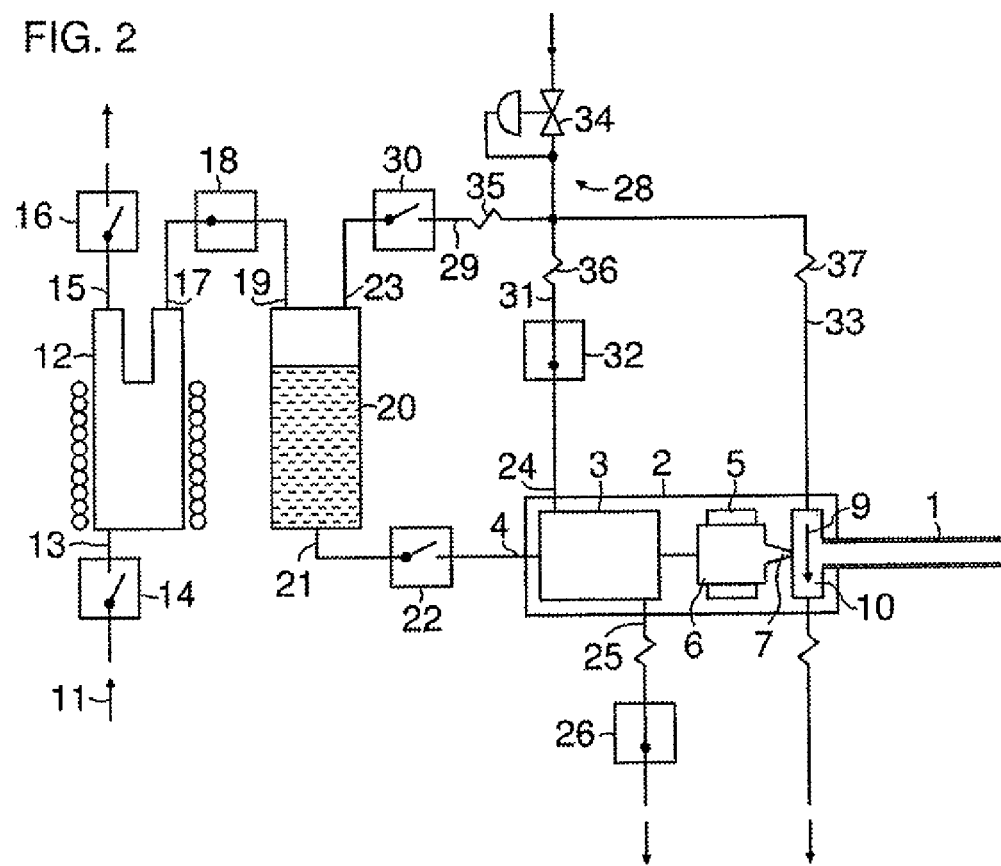

FIG. 2 shows the second phase, in which the third, fifth, and seventh valves 18, 26, 32 are opened and the remaining valves 14, 16, 22, 30 are closed. The liquid 11 is vaporized in the vaporization chamber 12 and the resulting vapor or its condensate is conducted into the condensate chamber 20. The reservoir 3 and the displacement space 6 are simultaneously flushed using the gas.

Figure 3:
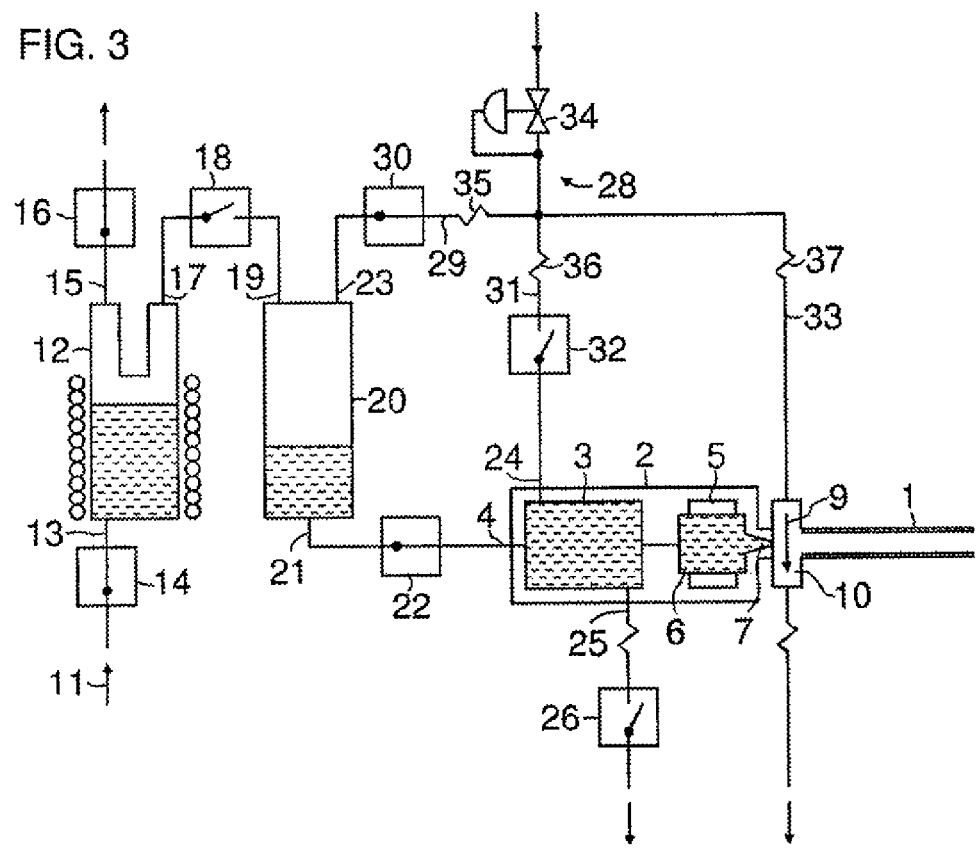

FIG. 3 shows the third phase, in which the first, second, fourth, and sixth valves 14, 16, 22, 30 are opened and the remaining valves 18, 26, 32 are closed. The liquid 11 to be metered again flows through the vaporization chamber 12, wherein residues remaining from the preceding vaporization phase, such as dissolved components which cannot be vaporized, are transported out of the chamber 12. Simultaneously, the reservoir 3 and the displacement space 6 are filled using the condensate from the condensate chamber 20.

Figure 4:
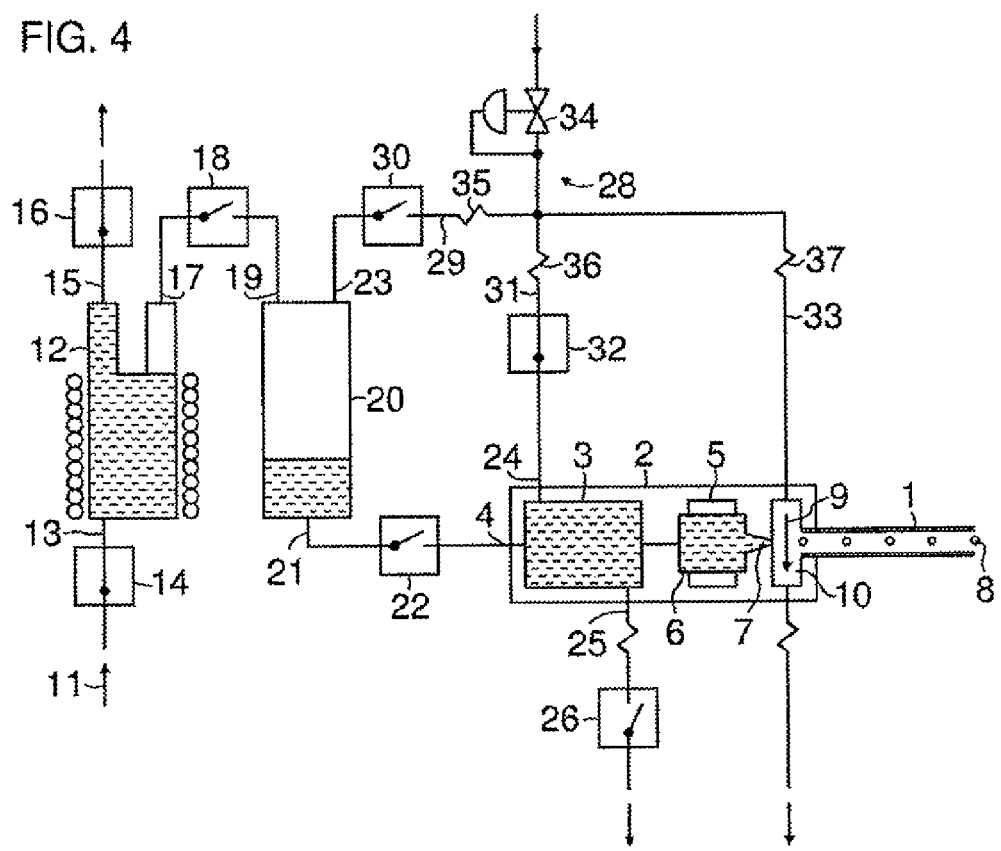

FIG. 4 shows the fourth phase, in which the first, second, and seventh valves 14, 16, 32 are opened and the remaining valves 18, 22, 26, 30 are closed. The liquid 11 to be metered flows through the vaporization chamber 12. The liquid droplets 8 are generated simultaneously, where the pressure in the reservoir 3 is kept constant by the pressure regulating unit 28.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A liquid metering device for a gas analyzer, comprising:
a gas source;
a droplet generator comprising a reservoir, an electromechanical transducer, a liquid inlet, an outlet opening and a displacement space connected to the reservoir and modifiable by electromechanical transducer, the displacement space shooting a liquid droplet through or counter to a gas stream generated by the gas source from a cold area into a heatable area upon excitation of the transducer;
a heatable vaporization chamber comprising, for a liquid to be metered, a liquid supply having a first valve, a liquid drain having a second valve, and a vapor outlet; and
a condensate chamber comprising a vapor or condensate inlet connected to the vapor outlet by a third valve, a condensate outlet and a gas inlet, the condensate outlet being connected by a fourth valve to the liquid inlet of the reservoir of the droplet generator, and the reservoir of the droplet generator including a liquid outlet having a fifth valve, and a gas inlet; and
a pressure regulating unit connected at a first outlet by a sixth valve to the gas inlet of the condensate chamber;
wherein the gas source is connected to a second outlet by a seventh valve to the gas inlet of the reservoir of the droplet generator, and provides the gas stream at a third outlet.

2. The liquid metering device as claimed in claim 1, wherein the pressure regulating unit includes a pressure regulator, which is connected via three flow resistances to the first, second and third outlets of the pressure regulating unit.

3. The liquid metering device as claimed in claim 2, further comprising:
a control unit which controls the first, second, third, fourth, fifth, sixth, and seventh valves;
wherein the control unit is configured to, in a first phase, open the first, second, fourth, fifth, and sixth valves and close the third and seventh valves to fill the vaporization chamber with the liquid to be metered and to flush the condensate chamber, the reservoir, and the displacement space with the gas;
wherein the control unit is configured to, in a second phase, open the third, fifth, and seventh valves and close the first, second, fourth and sixth valves to conduct vapor arising during vaporization of the liquid into the vaporization chamber or to conduct condensate vapor arising during vaporization of the liquid into the condensate chamber;
wherein the control unit is configured to, in a third phase, open the fourth and sixth valves and closing the third, fifth, and sixth valves to fill the reservoir and the displacement space with the condensate from the condensate chamber; and
wherein the control unit is configured to in a fourth phase, open the seventh valve and closing the third, fourth, fifth, and sixth valves to set a defined pressure in the reservoir during generation of the liquid droplet.

4. The liquid metering device as claimed in claim 1, further comprising:
a control unit which controls the first, second, third, fourth, fifth, sixth, and seventh valves;
wherein the control unit is configured to, in a first phase, open the first, second, fourth, fifth, and sixth valves and close the third and seventh valves to fill the vaporization chamber with the liquid to be metered and to flush the condensate chamber, the reservoir, and the displacement space with the gas;
wherein the control unit is configured to, in a second phase, open the third, fifth, and seventh valves and close the first, second, fourth and sixth valves to conduct vapor arising during vaporization of the liquid into the vaporization chamber or to conduct condensate vapor arising during vaporization of the liquid into the condensate chamber;
wherein the control unit is configured to, in a third phase, open the fourth and sixth valves and closing the third, fifth, and sixth valves to fill the reservoir and the displacement space with the condensate from the condensate chamber; and
wherein the control unit is configured to, in a fourth phase, open the seventh valve and closing the third, fourth, fifth, and sixth valves to set a defined pressure in the reservoir during generation of the liquid droplet.

5. The liquid metering device as claimed in claim 4, wherein the control unit is further configured to open the first and second valves in at least one of the third phase and the fourth phase to cause the liquid to flow through the vaporization chamber.

* * * * *